United States Patent
Haeuser

(10) Patent No.: US 10,224,118 B2
(45) Date of Patent: Mar. 5, 2019

(54) METHOD AND SYSTEM FOR CHECKING THE COMPATIBILITY OF DEVICE COMPONENTS OF A MEDICAL DEVICE

(71) Applicant: Siemens Healthcare GmbH, Erlangen (DE)

(72) Inventor: Peter Haeuser, Effeltrich (DE)

(73) Assignee: Siemens Healthcare GmbH, Erlangen (DE)

(*) Notice: Subject to any disclaimer, the term of this patent is extended or adjusted under 35 U.S.C. 154(b) by 282 days.

(21) Appl. No.: 15/183,972

(22) Filed: Jun. 16, 2016

(65) Prior Publication Data
US 2016/0371442 A1 Dec. 22, 2016

(30) Foreign Application Priority Data
Jun. 16, 2015 (DE) .................. 10 2015 211 036

(51) Int. Cl.
*G06F 19/00* (2018.01)
*G16H 40/20* (2018.01)
*G16H 40/40* (2018.01)

(52) U.S. Cl.
CPC ............. *G16H 40/40* (2018.01); *G06F 19/00* (2013.01); *G16H 40/20* (2018.01)

(58) Field of Classification Search
CPC ............................... G16H 40/40; G16H 40/20
See application file for complete search history.

(56) References Cited

U.S. PATENT DOCUMENTS

| | | | | |
|---|---|---|---|---|
| 5,579,509 A | * | 11/1996 | Furtney | ............... G06F 8/71 703/27 |
| 6,655,779 B2 | * | 12/2003 | Usui | ............... B41J 2/17546 347/19 |
| 6,898,768 B1 | * | 5/2005 | Theodossy | ............... G06F 8/65 703/27 |

(Continued)

FOREIGN PATENT DOCUMENTS

| | | |
|---|---|---|
| CN | 1837836 A | 9/2006 |
| CN | 102664044 A | 9/2012 |

(Continued)

OTHER PUBLICATIONS

Chinese Office Action for Application No. 201610352068.5, dated May 22, 2018 (with English translation).

*Primary Examiner* — Glenn A. Auve
(74) *Attorney, Agent, or Firm* — Schiff Hardin LLP

(57) ABSTRACT

A compatibility checking mechanism can include a reader, a checking mechanism, a writer and an approver. The reader can read out memory content from a memory of a first device component. The checking mechanism can check whether the first device component can be used together with a second device component based on the read-out memory content, and supply a result of the checking whether the first device component can be used together with a second device component. The writer can induce writing of a component identifier of the second device component in the memory of the first device component if checking of the read-out memory content indicates that the first device component can be used together with the second device component. The approver can approve or block use of the first device component as a function of the result of the checking of the read-out memory content.

10 Claims, 2 Drawing Sheets

(56) References Cited

U.S. PATENT DOCUMENTS

Figure 1:
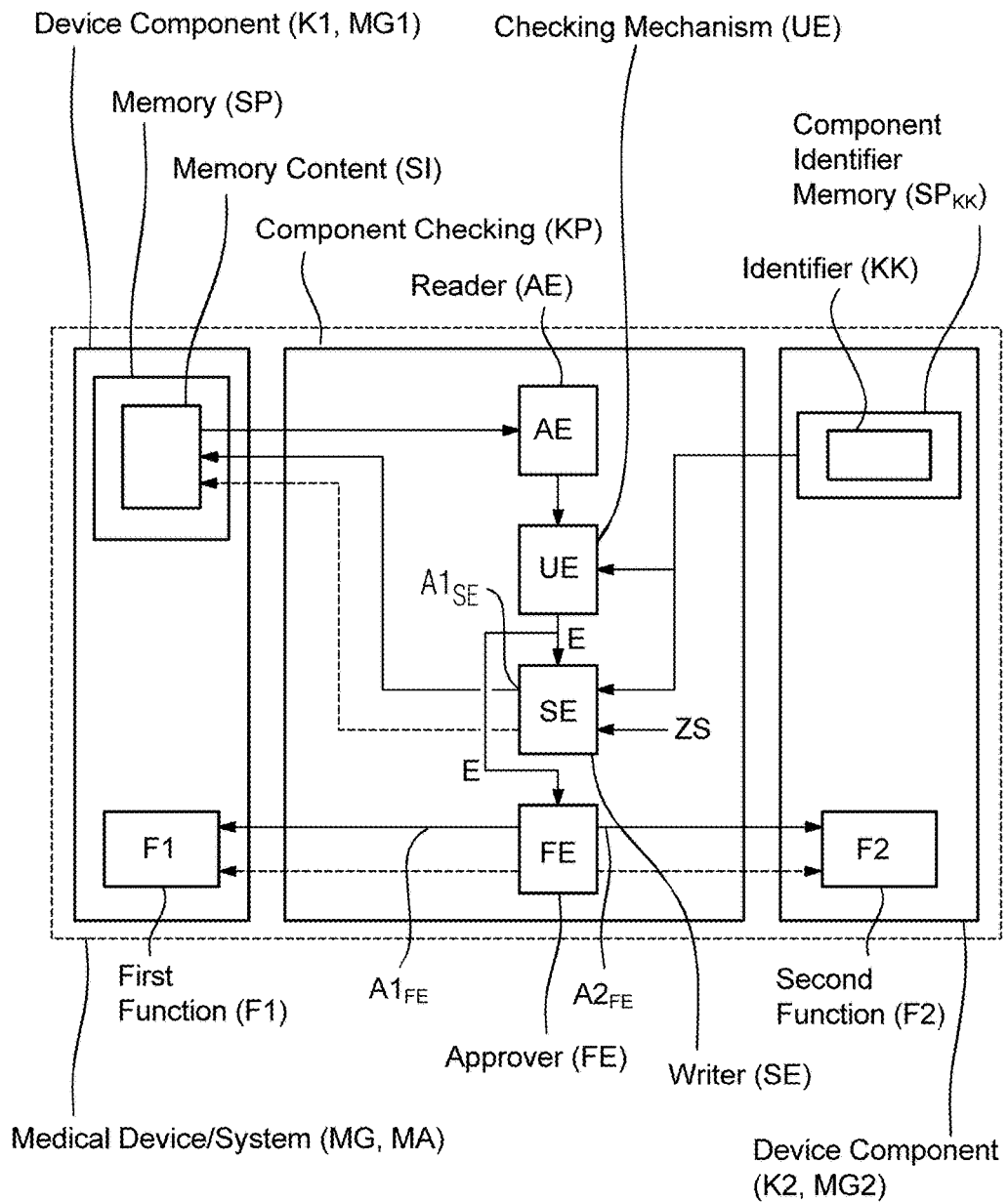

| | | | |
|---|---|---|---|
| 2006/0069824 A1* | 3/2006 | Hodder | G06F 3/1207 710/72 |
| 2006/0214795 A1 | 9/2006 | Kim | |
| 2007/0096691 A1* | 5/2007 | Duncan | G06F 1/263 320/114 |
| 2007/0282175 A1* | 12/2007 | Urbaszek | A61B 5/0031 600/300 |
| 2007/0284429 A1* | 12/2007 | Beeman | G06F 8/61 235/375 |
| 2012/0095315 A1* | 4/2012 | Tenbarge | A61B 5/7475 600/365 |
| 2012/0177020 A1* | 7/2012 | Chou | H04W 76/20 370/338 |
| 2013/0132416 A1* | 5/2013 | Hayter | G06F 19/32 707/758 |
| 2014/0055233 A1 | 2/2014 | Vetrivel et al. | |
| 2014/0163919 A1 | 6/2014 | Manigel et al. | |
| 2015/0121358 A1* | 4/2015 | Nekoonnarann | G06F 8/654 717/170 |
| 2015/0182694 A1* | 7/2015 | Rosinko | A61M 5/14244 604/151 |
| 2015/0199487 A1* | 7/2015 | Grauds | G06F 19/3406 235/375 |
| 2016/0188695 A1* | 6/2016 | Lee | G06F 8/60 707/738 |
| 2017/0064431 A1* | 3/2017 | Lee | H04R 5/04 |

FOREIGN PATENT DOCUMENTS

| | | |
|---|---|---|
| CN | 103116690 A | 5/2013 |
| CN | 103632027 A | 3/2014 |
| CN | 103845776 A | 6/2014 |
| DE | 10110758 A1 | 11/2002 |
| EP | 2110766 A1 | 10/2009 |

\* cited by examiner

METHOD AND SYSTEM FOR CHECKING THE COMPATIBILITY OF DEVICE COMPONENTS OF A MEDICAL DEVICE

CROSS REFERENCE TO RELATED APPLICATIONS

This patent application claims priority to German Patent Application No. 102015211036.2, filed Jun. 16, 2015, which is incorporated herein by reference in its entirety.

BACKGROUND

German Patent Application DE 10110758A1 proposes replacing a defective control device of a medical device with a control device blank, and, when a trigger condition is present, transmitting at least some of the programs and data of the defective control device to the control device blank and storing it there. In addition, the following optional developments are mentioned: disclosing the control device blank as an authorized control device blank, so only authorized control device blanks can access programs and data which are present in the control device; storing the time of data transmission in the control device and/or control device blank; deactivation of the defective control device following conclusion of data transmission, so its transmitting part does not transmit the available programs and data again; deactivation of a receiving function of the control device blank with the result that the control device blank cannot operate as a blank again. German Patent Application DE 10110758A1 is incorporated herein by reference in its entirety.

This method has the drawback that the manufacturer is not put in a position to be able to determine whether a replacement part, which was installed in a medical device by an external company, is being used in the medical device for the first time (i.e. directly after it was supplied by the manufacturer) or whether it has been disassembled from a different (for example from a withdrawn) medical device. Replacement parts which are installed in a housing, can be provided with a seal. Since companies (in-house and external), who are authorized by the manufacturer, have to open the housing for certain servicing or repair work, a damaged device seal could only prove a non-original state of the device component if all authorized servicing companies were equipped with devices seals for re-sealing. Distribution of device seals among authorized servicing companies cannot always be carried out for organizational reasons, or is undesirable.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 2:
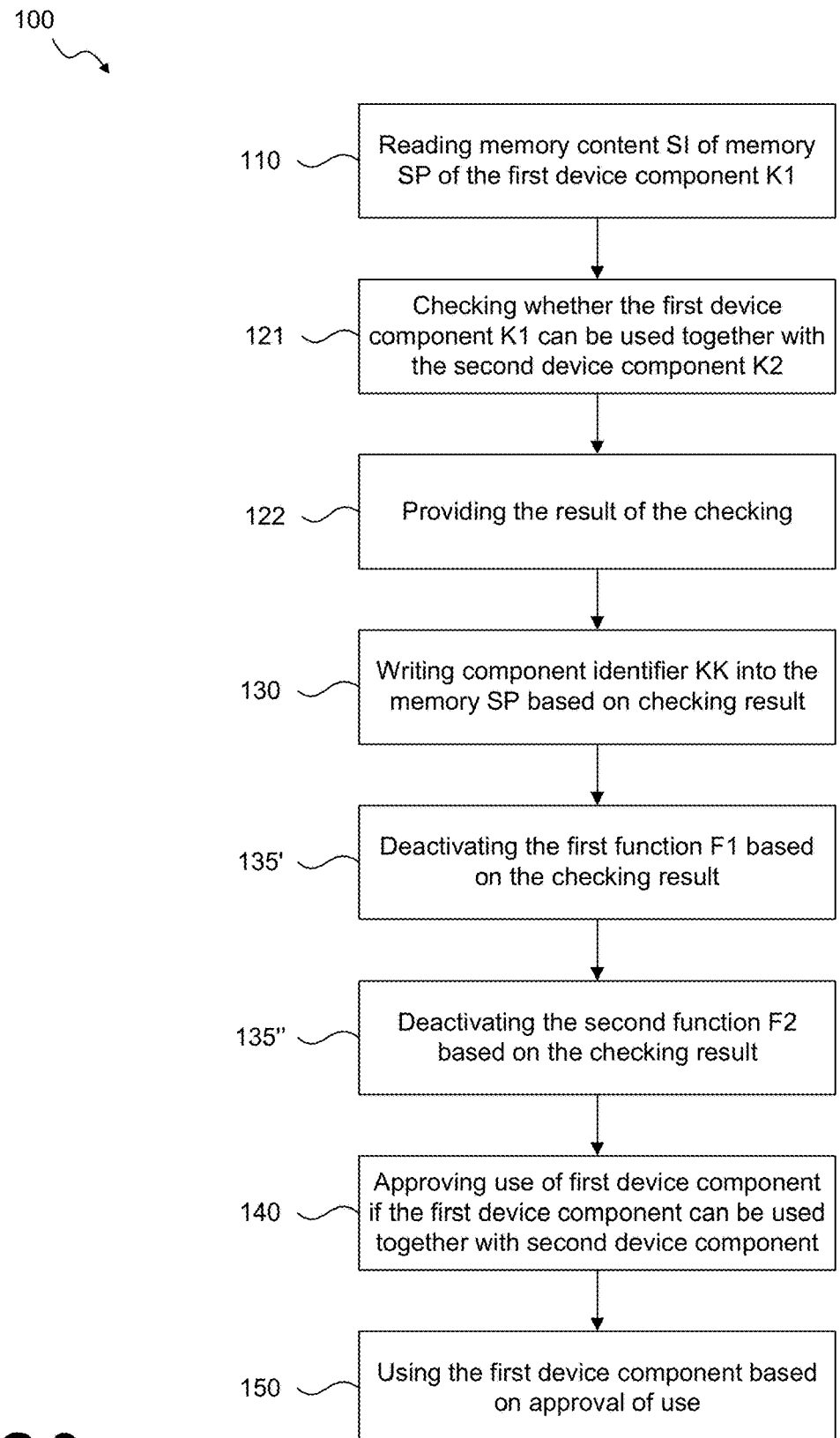

FIG. 1 shows a schematic block diagram of a medical device according to an exemplary embodiment of the present disclosure, and FIG. 2 schematically shows a flowchart of a method for checking the compatibility of a first device component with a second device component according to an exemplary embodiment of the present disclosure.

The exemplary embodiments of the present disclosure will be described with reference to the accompanying drawings.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

The present disclosure relates to a compatibility checking mechanism that can include a reader, a checking mechanism and an approver. The reader can be configured to read out memory content from a memory of a first device component. The checking mechanism can be configured to check with the aid of the read-out memory content whether the first device component can be used together with the second device component, and to supply a result of this checking. The approver can be configured to approve or block use of the first device component as a function of the result of checking. The first device component can be, for example, an assembly having a radiation source, an image intensifier or an image sensor. The second device component can be, for example, an assembly for a control device of a medical device. The first and second device components can also be a first and a second medical device whose compatibility is to be checked and which form a medical system when used together. One embodiment, not explicitly shown in the figures, provides that the second device component comprises the component checking mechanism.

The disclosure also relates to a medical device or to a medical system which has a compatibility checking mechanism of this kind. The medical device can be, for example, a computer tomograph, a magnetic resonance tomograph, an ultrasound device, a radiotherapy device, an endoscopy device or a treatment chair.

The disclosure also relates to a corresponding method for checking the compatibility of a first device component with a second device component.

Increasingly higher demands are being made of the quality of medical devices in particular in clinical diagnostics and treatment. The particular aim thereby is to avoid health risks and personal injuries as a consequence of incorrect diagnosis or treatment.

Since the repair and servicing of medical devices is still profitable, more and more external companies offer these services. Work results rendered by external companies frequently do not satisfy the inspection specifications and quality guidelines of the manufacturer of the respective medical device, however. This is due, inter alia, to the fact that external providers remove device components from old, withdrawn medical devices in order to install these device components in medical devices, which are to be repaired or serviced, for the purpose of troubleshooting.

If the device operator (for example following difficulties with the external provider) wants to hand over the servicing and repair of a medical device to the manufacturer again, the manufacturer cannot readily determine which of the replacement parts installed in the system are original parts and which are not. A risk of shifting responsibility for servicing and repair work, which has been carried out by one or more external companies, to the manufacturer follows from this uncertainty. This shifting of responsibility from an external company to the manufacturer is associated with an incalculable liability risk for the manufacturer.

For manufacturers of medical devices it is important to know the system configuration that is actually present (i.e. the inventory of preferably all device components that are actually installed, including all installed replacement parts) for each medical device at any time so, in the event of a fault, the disruption can be purposefully and quickly rectified and/or the operator of the device can be informed quickly and/or can be expediently advised.

To ensure this, automatic recognition of device components, which are connected by an interface to or in a medical device, can be provided in new generations of products for the health sector. The same applies to medical devices (instead of device components) which can be connected for the purpose of interaction with at least one other further medical device or can be integrated in a medical system. The information about the known, connected device components (or connected medical devices) is collated in a central computer of the medical device and with any change in the system configuration of the medical device or the medical system (for example on the occasion of replacement of a device component of the medical device) is transmitted via a data connection to a server of the manufacturer.

In addition, there can be the requirement for automatically recognizing device components whose mechanical device interfaces have the same construction but nevertheless have different electronic specifications, and can therefore only be used in specific medical devices (system types) so damage to the device or even personal injuries are avoided.

The difference in the device components can be based on information (for example a part number and/or a serial number and/or a version number) which is stored in a component of the device component (for example, in a memory such as an EPROM) and is read out from the installed device components (EPROM=erasable programmable read-only memory) with every booting of the medical device. Since even a main component of the medical device, in which the device components are installed, is identified by a part number and serial number and stored in the server of the manufacturer, device components of the main component (with which they can be used) can be clearly assigned. From the perspective of the present disclosure the main component of the medical device is, as a rule, the device component which will be called the second device component below.

It is an object of the present disclosure to provide a method with which the manufacturer of a medical device can establish even without using device seals whether a replacement part, which has been installed in a medical device, has been used in the medical device for the first time (i.e. virginally) (i.e. directly after it was supplied by the manufacturer) or whether it has been removed from another medical device (for example a withdrawn device).

This object is achieved according to an exemplary embodiment of the present disclosure using a compatibility checking mechanism. The compatibility checking mechanism can include a reader, a checking mechanism, a writer and an approver. The reader can be configured to read out memory content from a memory of a first device component. The checking mechanism can be configured to check with the aid of the read-out memory content whether the first device component can be used together with a second device component, and to supply a result of this checking. The writer can be configured to induce writing of a component identifier of the second device component in the memory of the first device component if checking of the read-out memory content has shown that the first device component can be used together with the second device component. The approver can be configured to approve or block use of the first device component as a function of the result of checking.

A method for checking the compatibility of a first device component with a second device component according to an exemplary embodiment is described. In an exemplary embodiment, the method includes: Firstly, memory content of a memory of the first device component is read out. Using the read-out memory content a check is then made as to whether the first device component can be together with the second device component, and a result of this checking is supplied. In a third method step a component identifier of the second device component is written in the memory of the first device component if checking has shown that the first device component can be used together with the second device component. In a fourth method step use of the first device component is approved as a function of the result of checking. The fourth method step can be performed before, after or at the same time as the third method step.

In an exemplary embodiment, a component identifier of the second device component is written in the memory of the first device component if checking has shown that the first device component can be used together with the second device component. It can hereby be ascertained at a later time, for example by authorized persons or the manufacturer (following the return of the first device component to the manufacturer) in which medical device the first device component has been used as intended.

In an exemplary embodiment, the checking mechanism is configured to approve joint use of the first and second device components if the read-out memory content does not comprise a component identifier. The first device component can be used for the first time in any medical device of a series belonging to the same manufacturer hereby if the first device component is even intended for operation in devices in this series.

In an exemplary embodiment, the checking mechanism can be configured to deny joint use of the first and second device components if memory content is stored in the memory but this memory content does not comprise the component identifier of the second device component. For this case it can expediently be provided that the device enters into a fault state and outputs a fault message to the operator of the device. If a first device component is returned to the manufacturer, the manufacturer can read out the memory of the first device component and determine whether the first device component has already been used together with a second device component and possibly with which one. By preventing use of the first device component together with the second device component if the memory content does not comprise the component identifier of the second device component, re-use or recycling of device components by external companies or persons who are not qualified by the manufacturer can be prevented. This applies at least as long as these external companies and persons do not know how the memory of a used device component may be put into a virginal state. For external companies and persons who have not been qualified by the manufacturer therefore, the business model of servicing medical devices against the will of the manufacturer with used device components, which are incorrectly refurbished or are not appropriate for the medical device, is made difficult.

In an exemplary embodiment, the writer is configured to not induce writing of the component identifier of the second device component in the memory if the read-out memory content already comprises a component identifier. As a result of this the component identifier of the second device component, with which the first device component was used for the first time, cannot be overwritten by means of simple installation and commissioning in a further device. Using the component identifier it is possible to determine the origin of the device component and, if this is deemed expedient, to initiate non-technical measures against the used trade in the device components.

In an exemplary embodiment, one user-friendly development results if the component identifier comprises a part number of the second device component. In an exemplary embodiment, alternatively or additionally, the component identifier can comprise a serial number of the second device component. A further possibility consists in the component identifier comprising a version number of the second device component. A possibility that is independent thereof is that the component identifier comprises a concealed value comprising the part number and/or a concealed value of the serial number and/or a concealed value of the version number. If the component identifier comprises a part number and/or version number, during commissioning of the first device component a check can be made using the part number as to whether the first device component is compatible with a second device component. If the component identifier comprises a serial number, during commissioning of the first device component a check can be made using the part number as to whether the first device component has already been used together with a second device component identical in construction (i.e. not dissimilar) but nevertheless different (i.e. separate).

In an exemplary embodiment, the writer is configured to induce writing of a time stamp in the memory of the first device component during writing of the component identifier of the second device component in the memory of the first device component. Using the time stamp the manufacturer can ascertain at a later time, for example by way of the device or following the return of the first device component to the manufacturer, a usage timeframe of the first device component which, for example, can answer the question of the existence or non-existence of guarantee claims.

In an exemplary embodiment, the method for checking the compatibility can comprise deactivation of a first function of the first device component if checking has shown that the first device component cannot be used together with the second device component. The first function can be, for example, a main function of the first device component. A main function should here be taken to mean a function for which the first device component is primarily intended. In the case of an X-ray apparatus this can be, for example, a replaceable assembly in which an X-ray tube is arranged. Deactivation of the first function can therefore increase the certainty that the medical device, or at least the first device component, can no longer be used for its main purpose and therefore a risk of personal injuries or damage to the device is reduced.

In an exemplary embodiment, alternatively or additionally, the method for checking the compatibility can comprise deactivation of a second function of the second device component if checking has shown that the first device component cannot be used together with the second device component. The second function can be, for example, a main function of the second device component. If a function of the second device component is deactivated by the attempt to use an inadmissible first device component in the medical device, analyses and manipulations of compatibility checking functions of the first and/or second device component(s) and/or the compatibility checking mechanism can be made considerably more difficult for such persons attempting to bypass the compatibility check.

In an exemplary embodiment, the method provides that the deactivation of the first function comprises deactivation of readability of the memory content of the memory of the first device component. Analyses and manipulations of compatibility checking functions of said device components for such persons attempting to bypass the compatibility checking are made considerably more difficult by this as well.

In an exemplary embodiment, alternatively or additionally, deactivation of the first function can comprise deactivation of a changeability of the memory content of the memory of the first device component. This means that the component identifier of the last admissible operating environment for the first device component cannot be overwritten, and following the return of the first device component the manufacturer can ascertain in which medical device the first device component was used as intended. The manufacturer can therefore determine the origin of the device component and, if this is deemed expedient, initiate non-technical measures against the used trade in device components.

In an exemplary embodiment, irrespective thereof, deactivation of the second function of the second device component can comprise deactivation of a first capability to read out the memory content of the first device component. Analyses and manipulations of recording and compatibility checking functions of the device components can be made considerably more difficult hereby for such persons attempting to bypass the compatibility checking. This development typically assumes that the second device component comprises the component checking mechanism.

In an exemplary embodiment, alternatively or additionally, deactivation of the second function of the second device component can comprise deactivation of a second capability to induce a change in the memory content of the first device component. Manipulation of the memory content of the memory of the first device component not intended by the manufacturer can be made more difficult as a result. This development also typically assumes that the second device component comprises the component checking mechanism.

In an exemplary embodiment, the medical device MG shown in FIG. 1 comprises a first device component K1, a second device component K2, a reader AE, a checking mechanism UE, a writer SE and an approver FE. The first device component K1 can be, for example, an assembly having a radiation source, an image intensifier or an image sensor. The second device component K2 can be, for example, an assembly for a control device of a medical device MG. The first K1 and second K2 device component can also be a first MG1 and a second medical device MG2 whose compatibility is to be checked and which form a medical system MA when used jointly. An embodiment not explicitly shown in the figures provides that the second device component K2 or the second medical device MG2 comprises the component checking mechanism KP. The component checking mechanism KP can be implemented in hardware (e.g., circuits), software, or a combination thereof In an exemplary embodiment, the component checking mechanism KP includes processor circuitry configured to perform one or more functions and/or operations of the component checking mechanism KP.

In an exemplary embodiment, the first device component K1 contains a memory SP for storing memory content SI. The second device component K2 contains a component identifier memory $SP_{KK}$ for storing a component identifier KK of the second device component K2. In an exemplary embodiment, the component identifier KK comprises a part number SN and/or a serial number SNR and/or a version number VNR and/or a concealed value H comprising the part number SN and/or the serial number SNR and/or the version number VNR. In an exemplary embodiment, the concealed value H can be a hash value of said values SN, SNR, VNR or a value H in which said values SN, SNR, VNR are mapped by means of a mapping rule which should expediently be kept secret. The compatibility checking method is particularly secure if the concealed value H includes redundancy.

In an exemplary embodiment, the reader AE can be connected to the memory SP of the first device component K1 and configured to read out the current memory content SI from the memory SP. The checking mechanism UE can be connected to an output of the reader AE. The reader AE can be configured to pass on the readout current memory content SI by way of its output to the checking mechanism UE. The checking mechanism UE is connected to an output of the component identifier memory $SP_{KK}$ to take over the component identifier KK of the second device component K2 from the component identifier memory $SP_{KK}$. The reader AE can be implemented in hardware (e.g., circuits), software, or a combination thereof In an exemplary embodiment, the reader AE includes processor circuitry configured to perform one or more functions and/or operations of the reader AE.

In an exemplary embodiment, the checking mechanism UE is configured to compare the current memory content SI with the component identifier KK and to decide whether operation of the first device component K1 together with the second device component K2 is admissible. The decision as to whether operation of the first device component K1 together with the second device component K2 is admissible can be a binary decision (a yes/no decision), but is not limited thereto. The checking mechanism UE passes the result of checking E to the writer SE and approver FE. The checking mechanism UE can be implemented in hardware (e.g., circuits), software, or a combination thereof In an exemplary embodiment, the checking mechanism UE includes processor circuitry configured to perform one or more functions and/or operations of the checking mechanism UE.

The writer SE is connected to an output of the component identifier memory $SP_{KK}$ to take over the component identifier KK of the second device component K2 from the component identifier memory $SP_{KK}$. The writer SE can be configured to write the component identifier KK into the memory content SI of the memory SP of the first device component K1 if the result of checking E contains the decision that operation of the first device component K1 together with the second device component K2 is admissible. Otherwise, the writer SE does not change at least the part of the memory content SI of the memory SP whose content is not compatible with the component identifier KK of the second device component K2.

In an exemplary embodiment, the writer SE can be configured to writes a time stamp ZS in the memory content SI of the memory SP of the first device component K1 only if the result of checking E contains the decision that operation of the first device component K1 together with the second device component K2 is admissible (see broken line with arrow). The writer SE can be implemented in hardware (e.g., circuits), software, or a combination thereof. In an exemplary embodiment, the writer SE includes processor circuitry configured to perform one or more functions and/or operations of the writer SE.

In an exemplary embodiment, the approver FE is configured to issue the first device component K1, by way of a first output $A1_{FE}$ (which forms part of the approver FE), with the command to approve a first function F1 of the first device component K1 if the result of checking E contains the decision that operation of the first device component K1 together with the second device component K2 is admissible. Otherwise, the approver FE issues the first device component K1, by way of the first output $A1_{FE}$ (which forms part of the approver FE), with the command not to approve the first function F1 of the first device component K1. The approver FE can be implemented in hardware (e.g., circuits), software, or a combination thereof. In an exemplary embodiment, the approver FE includes processor circuitry configured to perform one or more functions and/or operations of the approver FE.

In an exemplary embodiment, alternatively or additionally, the approver FE is configured to issue the second device component K2, by way of a second output $A2_{FE}$ (which forms part of the approver FE), with the command to approve a second function F2 of the second device component K2 if the result of checking E contains the decision that operation of the first device component K1 together with the second device component K2 is admissible. Otherwise, the approver FE issues the second device component K2, by way of the second output $A2_{FE}$ (which forms part of the approver FE), with the command to not approve the second function F2 of the second device component K2.

In an exemplary embodiment, the checking mechanism UE is configured to approve use of the first device component K1 together with the second device component K2 if the read-out memory content SI does not comprise a component identifier KK. The first device component K1 can hereby basically be used for the first time in any medical device MG of a series from the same manufacturer if the first device component K1 is even intended for operation in medical devices of this series.

In an exemplary embodiment, the checking mechanism UE can be configured to deny use of the first device component K1 together with the second device component K2 if memory content SI is stored in the memory SP but this memory content SI does not comprise the component identifier KK of the second device component K2. For this case it can expediently be provided that the medical device MG enters into a fault state and outputs a fault message to the operator of the medical device MG. If a first device component K1 is returned to the manufacturer, the manufacturer can read out the memory SP of the first device component K1 and determine whether the first device component K1 has already been used with a second device component K2 and possibly with which one. As soon as a first device component K1 returned to the manufacturer has been checked and, if required, repaired or recycled, the memory content SI can be deleted and the first device component K1 used again in any suitable medical device MG.

In an exemplary embodiment, a particular feature or exception are coils of magnetic resonance tomography devices or ultrasound devices since the user can conventionally also use these coils on different devices and these coils are not permanently connected to the system either. In an exemplary embodiment, a different solution can be provided for these coils, such as, for example, a mechanical seal, or a mechanism which opens a contact when the coil is opened and thereby deletes the content of a memory, such as an EPROM.

In an exemplary embodiment, the writer SE can be configured to not induce writing of the component identifier KK of the second device component K1 in the memory SP if the read-out memory content SI already comprises a component identifier KK. This means that the component identifier KK of the second device component K2, with which the first device component K1 was used for the first time, cannot be overwritten by simple installation and commissioning in a further device. Using the component identifier KK it is possible to determine the origin of the first device component K1 and, if this is deemed expedient, to also initiate non-technical measures against the used trade in device components.

FIG. 2 illustrates the method 100 for checking the compatibility of a first device component K1 with a second device component K2 according to an exemplary embodiment of the present disclosure. The method can include memory content SI of a memory SP of the first device component K1 being read out. A check is then made using the read-out memory content SI as to whether the first device component K1 can be used together with the second device component K2, and a result E of this checking 121 is supplied. In a third method step 130, a component identifier KK of the second device component K2 is written into the memory SP if checking 121 has shown that the first device component K1 can be used together with the second device component K2. In a fourth method step 140 use 150 of the first device component K1 is approved as a function of the result E of checking 121. The fourth method step 140 can be performed before, after or at the same time as the third method step 130.

In an exemplary embodiment, the method 100 can include a first function F1 of the first device component K1 being deactivated and/or a second function F2 of the second device component K2 being deactivated if the check 120 has shown that the first device component K1 cannot be used together with the second device component K2.

In an exemplary embodiment, the deactivation 135' of the first function F1 comprises deactivation of readability and/or deactivation of a changeability of the memory content SI of the memory SP of the first device component K1. Alternatively or additionally, deactivation 135" of the second function F2 comprises deactivation of a first capability to read out the memory content SI of the first device component K1 and/or deactivation of a second capability to induce a change in the memory content SI of the first device component K1.

In an exemplary embodiment, the disclosure provides a compatibility checking mechanism KP that includes: a reader AE for reading out memory content SI from a memory SP of a first device component K1, a checking mechanism UE for checking using the read-out memory content SI and a writer SE for inducing writing of a component identifier KK of the second device component K2 in the memory SP if the first device component K1 can be used together with the second device component K2. The compatibility checking mechanism also has an approver FE which can be configured to approve use 150 of the first device component K1 if the first device component K1 can be used together with the second device component K2.

If, following unsuccessful service by an external company, the user asks the manufacturer of the medical device MG to repair the medical device, the manufacturer can assume with a degree of certainty that only originally checked parts have been installed in the system, whereby liability risks described in the introduction are reduced.

CONCLUSION

The aforementioned description of the specific embodiments will so fully reveal the general nature of the disclosure that others can, by applying knowledge within the skill of the art, readily modify and/or adapt for various applications such specific embodiments, without undue experimentation, and without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof Embodiments may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, processor circuitry can include one or more circuits, one or more processors, logic, or a combination thereof For example, a circuit can include an analog circuit, a digital circuit, state machine logic, other structural electronic hardware, or a combination thereof A processor can include a microprocessor, a digital signal processor (DSP), or other hardware processor. In one or more exemplary embodiments, the processor can include a memory, and the processor can be "hard-coded" with instructions to perform corresponding function(s) according to embodiments described herein. In these examples, the hard-coded instructions can be stored on the memory. Alternatively or additionally, the processor can access an internal and/or external memory to retrieve instructions stored in the internal and/or external memory, which when executed by the processor, perform the corresponding function(s) associated with the processor, and/or one or more functions and/or operations related to the operation of a component having the processor included therein.

In one or more of the exemplary embodiments described herein, memory can be any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable or removable.

What is claimed is:

1. A compatibility checking mechanism comprising:
   a reader configured to read out memory content from a memory of a first device component;
   a checking mechanism configured to:
      check whether the first device component can be used together with a second device component based on the read-out memory content, and
      supply a result of the checking whether the first device component can be used together with a second device component;
   a writer configured to induce writing of a component identifier of the second device component in the memory of the first device component if checking of the read-out memory content indicates that the first device component can be used together with the second device component; and
   an approver configured to approve or block use of the first device component as a function of the result of the checking of the read-out memory content.

2. The compatibility checking mechanism according to claim 1, wherein the checking mechanism is configured to approve joint use of the first and second device components if the read-out memory content does not comprise a component identifier.

3. The compatibility checking mechanism according to claim 1, wherein the checking mechanism is configured to deny joint use of the first and second device components if the memory content stored in the memory does not comprise the component identifier of the second device component.

4. The compatibility checking mechanism according to claim 1, wherein the writer is configured to not induce writing of the component identifier of the second device component in the memory if the read-out memory content already includes a component identifier.

5. The compatibility checking mechanism according to claim 1, wherein the component identifier comprises at least one of:
   a part number of the second device component,
   a serial number,
   a version number of the second device component, and
   a concealed value including at least one of the part number, the serial number, and the version number.

6. The compatibility checking mechanism according to claim 1, wherein, during writing of the component identifier of the second device component in the memory of the first device component, the writer is configured to induce writing of a time stamp in the memory of the first device component.

7. A medical device comprising the compatibility checking mechanism of claim 1.

8. A method for checking the compatibility of a first device component with a second device component, wherein the method comprises:
   reading out memory content of a memory of the first device component;
   checking, with the aid of the read-out memory content, whether the first device component can be used together with the second device component, and supplying a result of the checking whether the first device component can be used together with the second device component;
   writing a component identifier of the second device component in the memory of the first device component if checking indicates that the first device component can be used together with the second device component; and
   approving use of the first device component as a function of the result of checking.

9. The method according to claim 8, further comprising:
   deactivating at least one of a first function of the first device component and a second function of the second device component if checking indicates that the first device component cannot be used together with the second device component.

10. The method according to claim 9, wherein:
    deactivation of the first function comprises at least one of deactivating a readability of the memory content of the memory of the first device component, and deactivating a changeability of the memory content of the memory of the first device component, and
    deactivation of the second function of the second device component comprises at least one of deactivating a first capability to read out the memory content of the first device component, and deactivating a second capability to induce a change in the memory content of the first device component.

* * * * *